(12) United States Patent
Jones

(10) Patent No.: US 11,099,407 B2
(45) Date of Patent: Aug. 24, 2021

(54) CONFIGURABLE EYEWEAR SYSTEM

(71) Applicant: Jennifer Jones, Mira Loma, CA (US)

(72) Inventor: Jennifer Jones, Mira Loma, CA (US)

(*) Notice: Subject to any disclaimer, the term of this patent is extended or adjusted under 35 U.S.C. 154(b) by 453 days.

(21) Appl. No.: 15/143,631

(22) Filed: May 2, 2016

(65) Prior Publication Data

US 2017/0315382 A1 Nov. 2, 2017

(51) Int. Cl.
*A61F 9/00* (2006.01)
*B29D 11/00* (2006.01)
*G02C 7/08* (2006.01)
*G02C 9/04* (2006.01)
*G02C 5/00* (2006.01)
*G06Q 30/06* (2012.01)
*G02C 5/02* (2006.01)
*G02C 5/14* (2006.01)

(52) U.S. Cl.
CPC .......... *G02C 7/086* (2013.01); *B29D 11/0024* (2013.01); *G02C 5/008* (2013.01); *G02C 9/04* (2013.01); *G06Q 30/0621* (2013.01); *G06Q 30/0643* (2013.01); *A61F 9/0061* (2013.01); *G02C 5/02* (2013.01); *G02C 5/14* (2013.01); *G02C 2200/02* (2013.01); *G02C 2200/06* (2013.01); *G02C 2200/16* (2013.01)

(58) Field of Classification Search
CPC ........ G02C 2200/02; G02C 9/00; G02C 9/04; A61F 9/0061; B29D 11/00038; B29D 11/00817; B29D 11/0024
USPC ....................................... 294/1.2; 351/57, 47
See application file for complete search history.

(56) References Cited

U.S. PATENT DOCUMENTS

| | | | | |
|---|---|---|---|---|
| 2,415,275 A * | 2/1947 | Bruckman | ............... | D06F 67/08 219/486 |
| 5,050,918 A * | 9/1991 | Kolze | ................... | A61F 9/0061 294/1.2 |
| 5,243,366 A * | 9/1993 | Blevins | .................... | G02C 7/06 351/57 |
| 5,407,241 A * | 4/1995 | Harrison | ............... | A61F 9/0061 206/5.1 |
| 5,598,232 A * | 1/1997 | Pronesti | ................... | G02C 7/06 351/54 |
| 5,838,417 A * | 11/1998 | Dahan | ...................... | G02C 9/04 351/42 |
| 6,154,929 A * | 12/2000 | Dwyer | .................... | B63B 17/00 16/422 |
| 10,265,214 B2 * | 4/2019 | Shulman | ............... | A61F 9/0008 |

(Continued)

*Primary Examiner* — Mahdi H Nejad
(74) *Attorney, Agent, or Firm* — The Law Office of Herbert T Patty

(57) ABSTRACT

The present disclosure relates to a novel eyewear system and a method to configure the same. An eyewear system consistent with the present disclosure comprises an eyewear frame and a lens casing attached thereto. The eyewear system comprises a set of insertable lenses fitted between said eyewear frame and said lens casing. The lens casing comprises a pliable material to receive the set of insertable lenses. Further, the present disclosure provides a method for a consumer to design and order a pair of eyewear using an online system. The method may include prompting a user to choose from a plurality of unique frame options. Based on the user's selection of the frame, display to the user a plurality of lens casing options. In addition, based on the user's selection of the lens casing options, associate the selected frame and the selected lens casing with a customer order.

10 Claims, 6 Drawing Sheets

(56) References Cited

U.S. PATENT DOCUMENTS

| | | | |
|---|---|---|---|
| 2004/0074525 A1* | 4/2004 | Widman | B29D 11/00067 |
| | | | 134/34 |
| 2006/0126006 A1* | 6/2006 | Smith | G02C 9/00 |
| | | | 351/47 |
| 2006/0192916 A1* | 8/2006 | Langley | G02C 1/02 |
| | | | 351/41 |
| 2007/0262596 A1* | 11/2007 | Renard | A61F 9/0026 |
| | | | 294/1.2 |
| 2014/0002789 A1* | 1/2014 | Pugh | G02B 3/14 |
| | | | 351/159.39 |
| 2015/0150416 A1* | 6/2015 | Hoare | A47J 43/0711 |
| | | | 366/344 |
| 2016/0120701 A1* | 5/2016 | Fujimoto | B63C 11/12 |
| | | | 2/431 |
| 2018/0344520 A1* | 12/2018 | Daniels | A61F 9/0061 |
| 2020/0064652 A1* | 2/2020 | Asemani | A42B 1/247 |

* cited by examiner

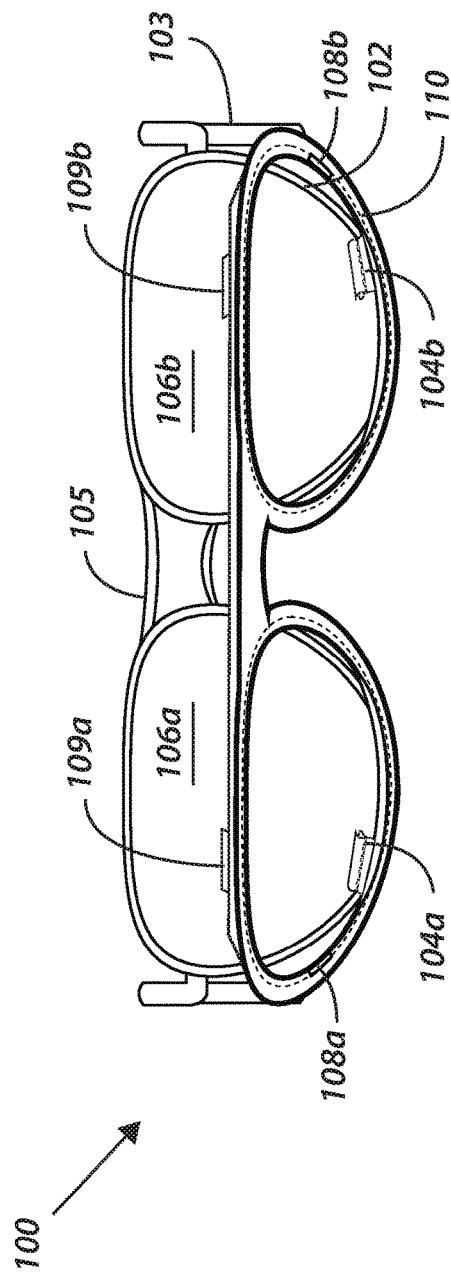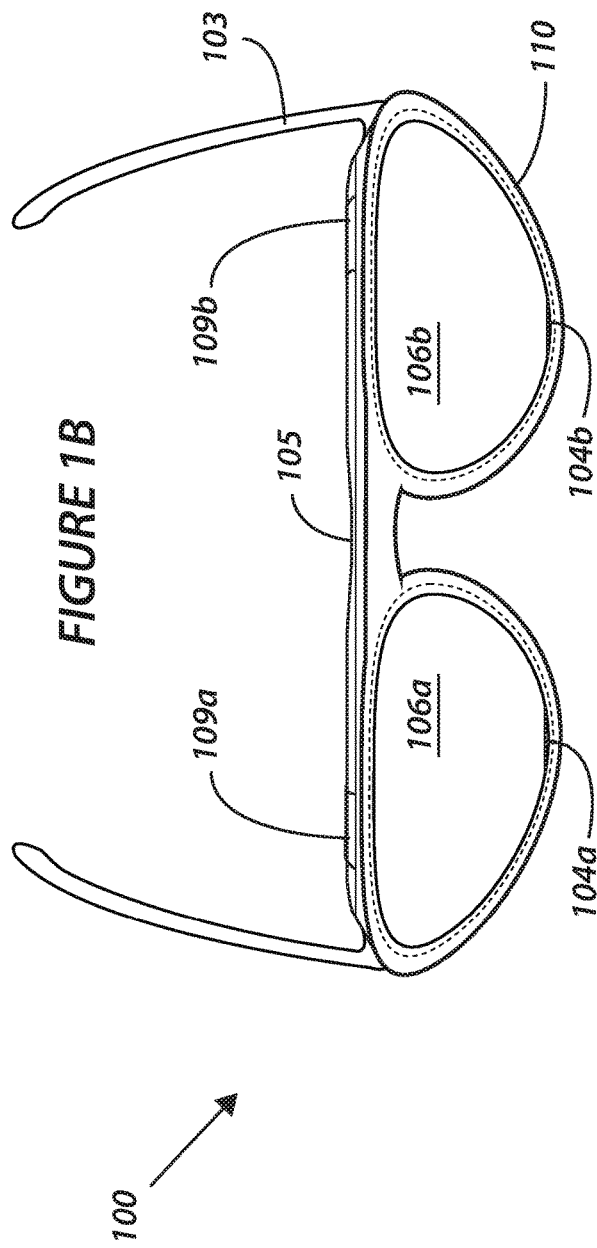

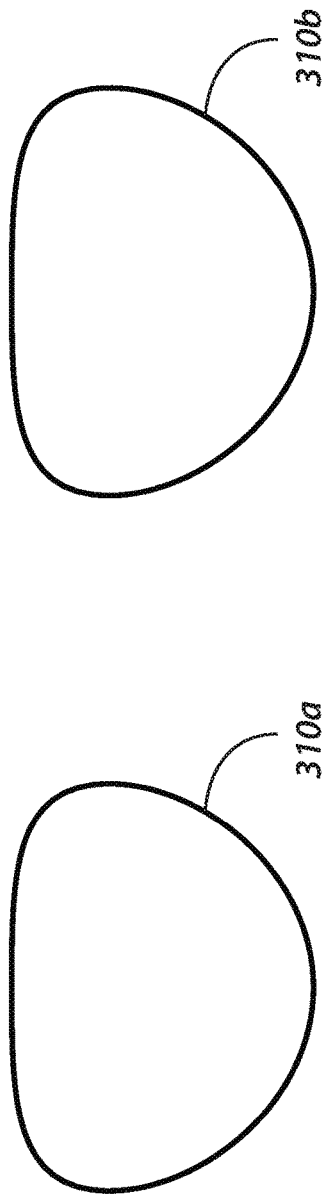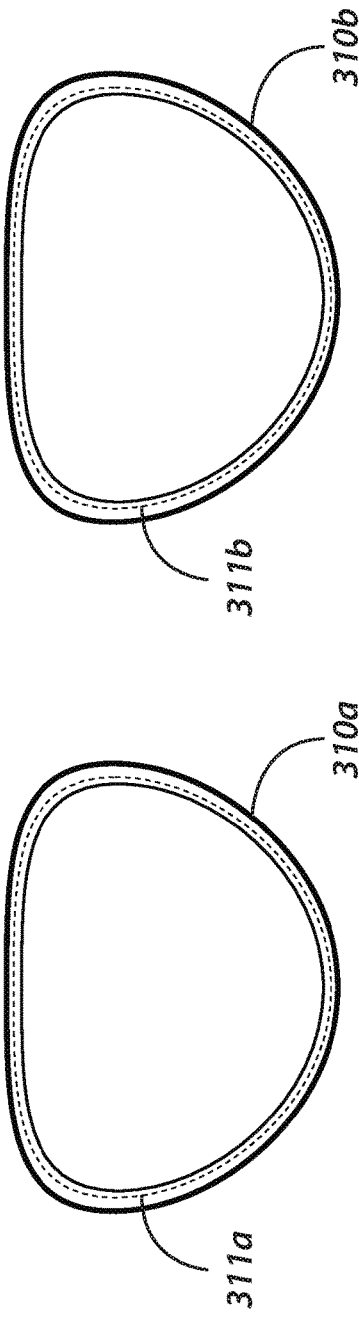

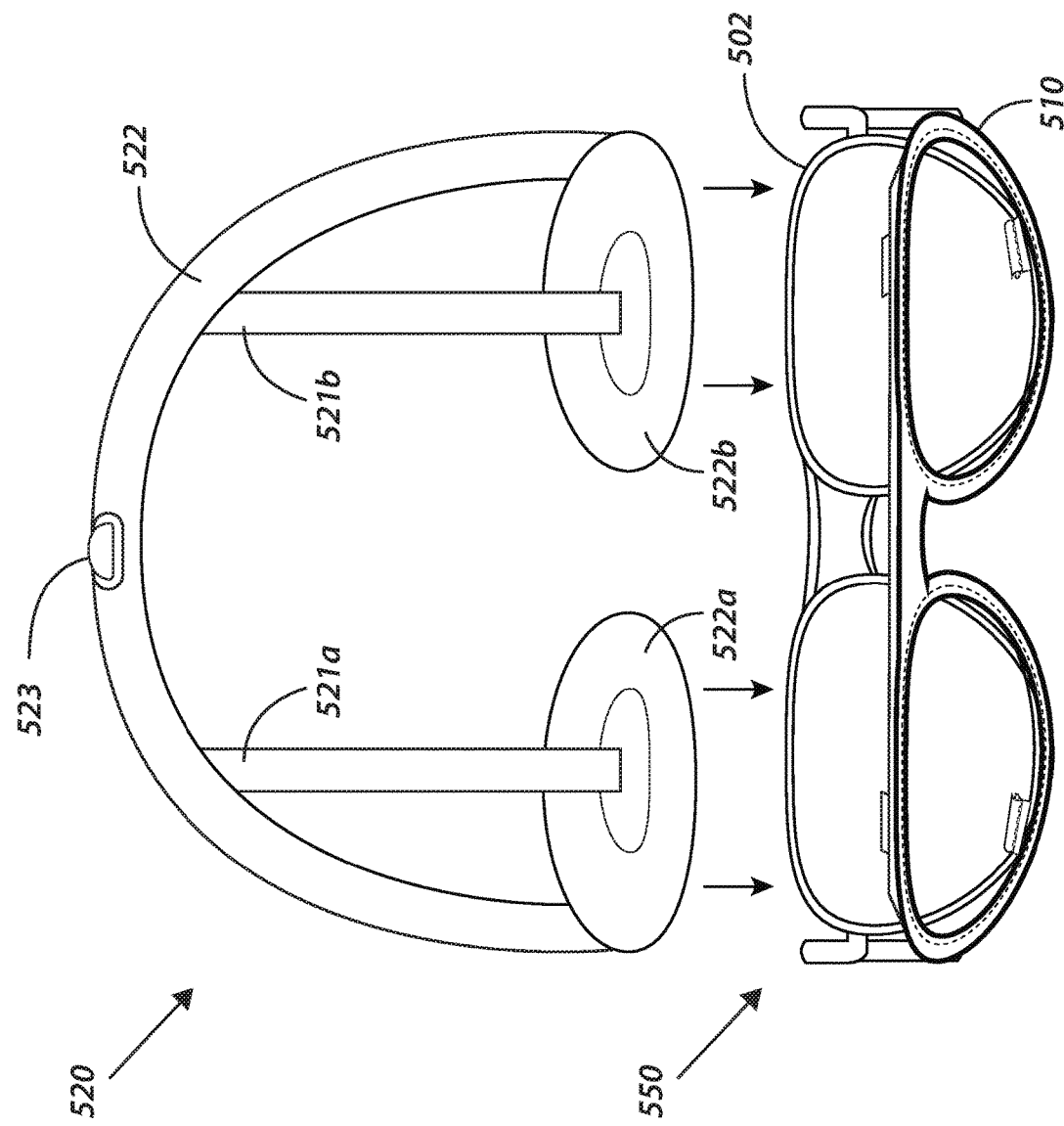

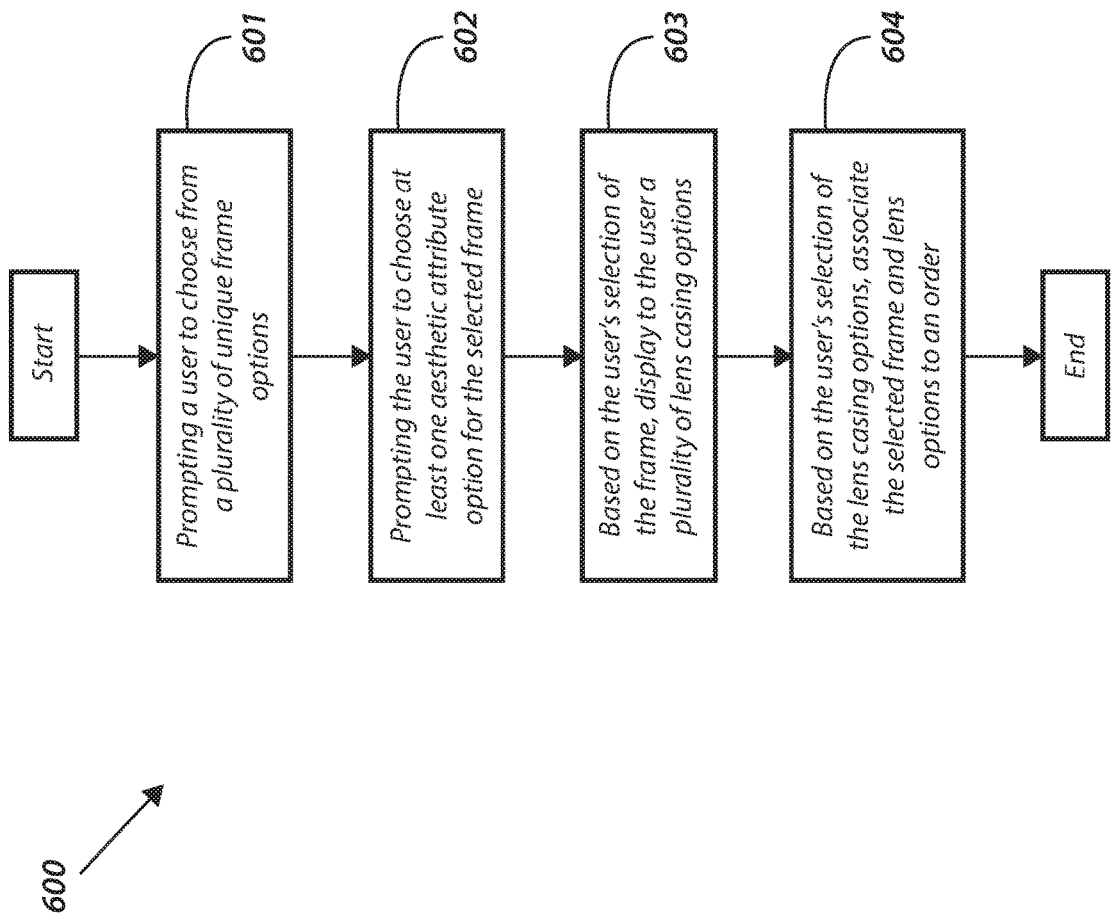

CONFIGURABLE EYEWEAR SYSTEM

FIELD OF THE DISCLOSURE

The present disclosure relates to a novel eyewear system and a method to configure the same.

BRIEF DESCRIPTION OF THE DRAWINGS

To facilitate understanding, identical reference numerals have been used, wherever possible, to designate identical elements that are common to the figures. The drawings are not to scale and the relative dimensions of various elements in the drawings are depicted schematically and not necessarily to scale. The techniques of the present disclosure may readily be understood by considering the following detailed description in conjunction with the accompanying drawings, in which:

FIG. 1A is a perspective diagram of a novel eyewear apparatus with a lens casing in an open position.

FIG. 1B is a perspective diagram of the novel eyewear apparatus with the lens casing in a closed position.

FIG. 3A depicts a front side of a set of insertable lenses consistent with the present disclosure.

FIG. 3B depicts a back side of a set of insertable lenses consistent with the present disclosure.

FIG. 5 is an exemplary illustration of a tool used to deliver a set of insertable lenses to the novel eyewear apparatus of the present disclosure.

FIG. 6 is a flowchart of a method for enabling a user to assemble an eyewear apparatus consistent with the present disclosure.

SUMMARY

Figure 2:
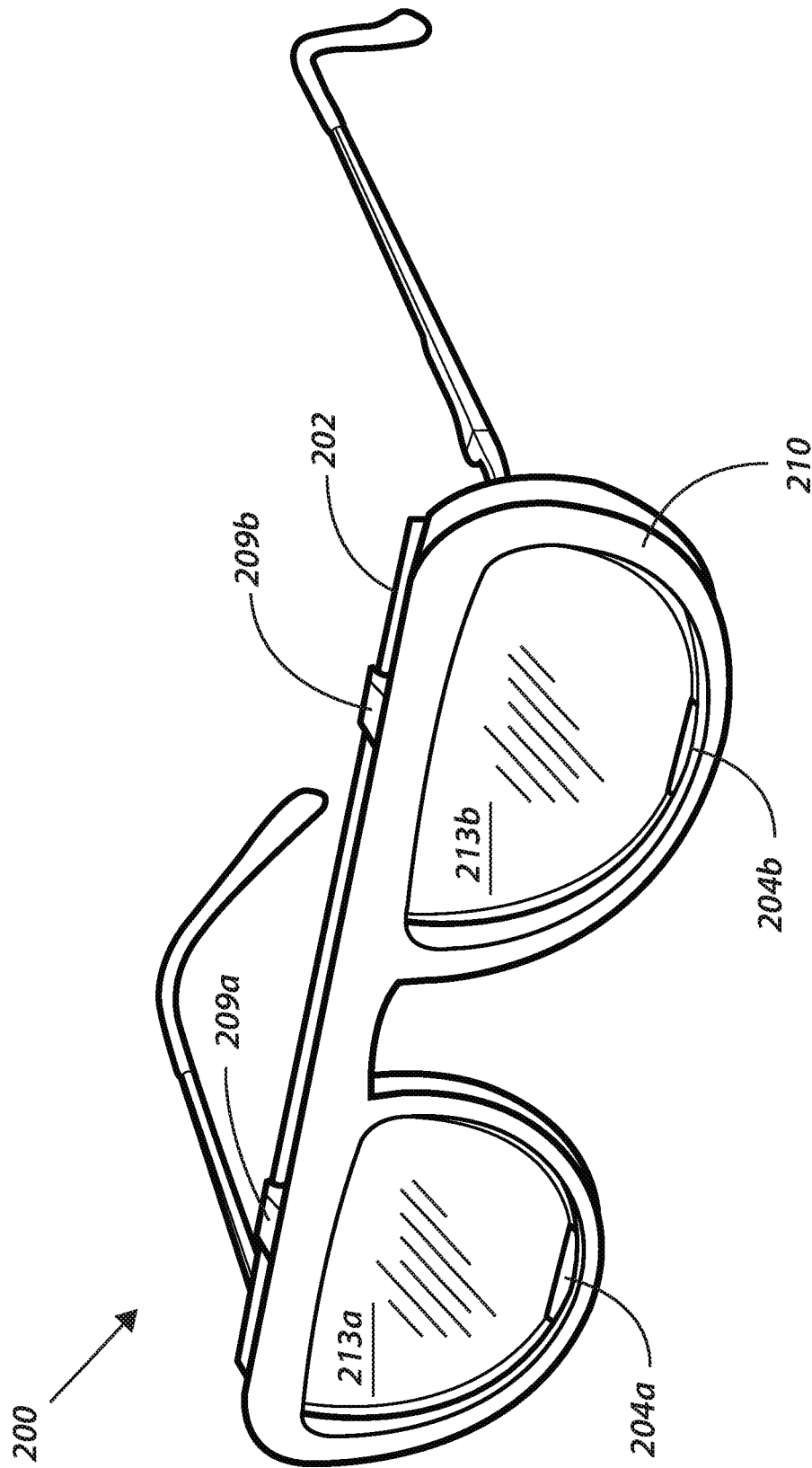
FIG. 2 is a perspective diagram of a novel eyewear apparatus with a permanently-attached lens casing.

The present disclosure relates to a novel eyewear system and a method to configure the same. An eyewear system consistent with the present disclosure comprises an eyewear frame and a lens casing attached thereto. The eyewear system comprises a set of insertable lenses fitted between said eyewear frame and said lens casing. The lens casing comprises a pliable material to receive the set of insertable lenses. Further, the present disclosure provides a method for a consumer to design and order a pair of eyewear using an online system. The method may include prompting a user to choose from a plurality of unique frame options. Based on the user's selection of the frame, display to the user a plurality of lens casing options. In addition, based on the user's selection of the lens casing options, associate the selected frame and the selected lens casing with a customer order.

DETAILED DESCRIPTION

Before the present disclosure is described in detail, it is to be understood that, unless otherwise indicated, this disclosure is not limited to specific procedures or articles, whether described or not.

It is further to be understood that the terminology used herein is for the purpose of describing particular embodiments only and is not intended to limit the scope of the present disclosure.

It must be noted that as used herein and in the claims, the singular forms "a," and "the" include plural referents unless the context clearly dictates otherwise. Thus, for example, reference to "an enclosure" also includes two or more enclosures, and so forth.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also included in the disclosure. The term "about" generally refers to ±10% of a stated value.

FIG. 1A is a perspective diagram of a novel eyewear system (eyewear 100) with a lens casing 110 in an open position. Eyewear 100 resembles a pair of conventional eyewear frames 102 with the addition of a lens casing 110 that is adjacent to lenses 106a, 106b. Consistent with conventional eyewear frames, eyewear 100 includes a set of lens 106a, 106b, a bridge 105, and a pair of temples 103. In some embodiments, set of lenses 106a, 106b are non-prescriptive lenses.

In some implementations, lens casing 110 is detachable from eyewear 100. Lens casing 110 may have any of various aesthetic designs such that lens casings 110 provides a variety of shapes and aesthetic attributes to eyewear 100. For example, lens casing 110 may be square-shaped and feature designs thereon or thereto. As such, a user's selection of a lens casing 110 can create a desired look or style that meets the personal taste of the user.

In some implementations, eyewear 100 includes a mechanism such that lens casing 110 can attach to a peripheral portion of eyewear 100. For example, in the embodiment shown, eyewear 100 includes components 104a, 104b to effect a snap connection to secure lens casing 110 to frame 102.

Components 104a, 104b may further function as a hinge such that lens casing 110 may deflect from eyewear frame 102. Accordingly, components 104a, 104b may be referred to as snap-hinge components 104a, 104b as they may allow lens casing 110 to be attached to and deflect from eyewear frame 102.

In addition, eyewear 1000 may further include additional snap connectors 109a, 109b which help couple lens casing 110 to eyewear frame 102. As such, in some embodiments, snap connectors 109a, 109b along with snap-hinge components 104a, 104b cooperate with each other to couple lens casing 110 to eyewear frame 102.

In the open position, eyewear 100 is configured to receive a set of insertable lenses (not shown) as will be described below. In some embodiments, the insertable lens may be a prescriptive pair of lens. Advantageously, the insertable lens may be assembled within eyewear 100 by any of various means. For example, insertable lens may be inserted manually within the eyewear 100. Alternatively, the set of insertable lenses may be inserted into eyewear 100 by utilizing a tool as will be discussed below.

When assembling the set of insertable lenses into eyewear 100, the lens may be guided by set of receiving components 108a, 108b. Set of receiving components 108a, 108b may comprise a pliable material to accommodate the fitting of various lens shapes. For example, receiving components 108a, 108 may comprise plastic, rubber, or other suitable materials.

When lens casing 110 is in an open position, lens casing 110 may be disposed approximately 45°-90° from eyewear frame 102. In other implementations, snap-hinge attachments 104a, 104b may allow lens casing 110 to deflect greater than 90° (e.g., 135°) from the eyewear frame 102.

FIG. 1B is a perspective diagram of a novel eyewear apparatus 100 with a lens casing 110 in a closed position. In the closed position, eyewear 100 can contain and retain a set of insertable lenses therein. As such, eyewear 100 may operate as a single eyewear system that meets the functional and aesthetic requirements of the owner. Advantageously, the owner can reconfigure eyewear 100 by swapping out lens casing 110 with a new casing. Alternatively, the owner can attach the lens casing 110 to a new eyewear frame 102.

FIG. 2 is a perspective diagram of a novel eyewear apparatus 200 with a permanently-attached lens casing 210. As depicted in the figure, lens casing 210 is permanently attached to eyewear frame 202. As will be described below, a user may select a lens casing based on a previous selection of an eyewear frame, or vice versa. Afterwards, the eyewear apparatus may be assembled such that the lens casing and the eyewear frame are coupled together by any suitable means known in the art.

For example, in the figure, eyewear 200 incorporates custom brackets 204a, 204b, 209a, 209b to couple lens casing 210 to eyewear frame 202 to form a unitary eyewear system 200. Most notably, eyewear 200 may contact a set of insertable lenses 213a, 213b therein to meet the visual needs of the owner.

FIG. 3A depicts a front side of a set of insertable lenses 310a, 310b that may be inserted within an eyewear system consistent with the present disclosure. Lens 310a, 310b may be prescription lenses.

FIG. 3B depicts a back side of a set of insertable lenses 310a, 310b. Notably, the figure exposes a magnetic strip disposed along the peripheral edge of the insertable lenses 310a, 310b. However, it should be understood by one having ordinary skill in the art that the present disclosure is not limited thereto.

As will be described in more detail below, magnetic regions 311a, 311b enable the set of insertable lenses 310a, 310b to be retrieved by a tool and assembled into a novel eyewear system.

Figure 4:
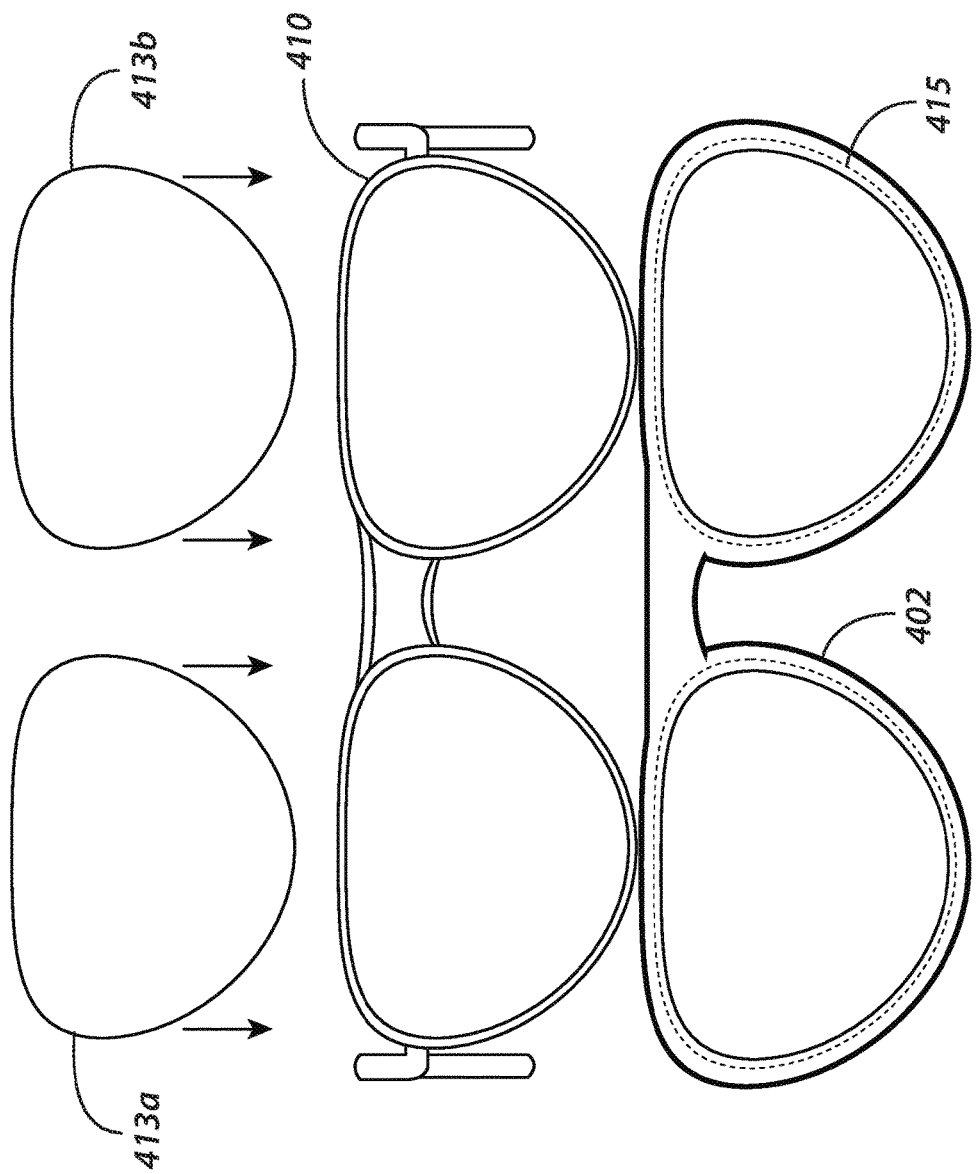
FIG. 4 is an exemplary illustration which depicts a direction in which a set of insertable lenses are assembled into the eyewear apparatus.

FIG. 4 is an exemplary illustration which depicts a direction in which a set of insertable lenses 413a, 413b are assembled into the novel eyewear system. In the embodiment, the set of insertable lenses 413a, 413b are inserted into the eyewear apparatus from the top of eyewear frame 402 and lens casing 410. In some embodiments, a magnetic strip 415 is disposed on a backside of lens casing 410.

FIG. 5 is an exemplary illustration of a tool 520 used to deliver a set of insertable lenses to the novel eyewear system. Tool 520 includes a handle 522 and one or more extensions 521a, 521b that extend therefrom when engaged. Tool 520 may include a mechanism (e.g., release button 523) to engage or disengage the extensions 521a, 521b. The extensions 521a, 521b may be spring loaded but the present disclosure is not limited thereto. In some implementations, tool 520 comprises mechanical, electrical, or pneumatic components known in the art to effect engagement or disengagement of the extensions 521a, 521b.

At the end of handle 522 are lens-coupling components 522a, 522b. In some implementations, lens-coupling components 522a, 522b may have a shape that meets the form factor of a set of insertable lenses (not shown). Lens-coupling components 522a, 522b may include a magnetic region on a bottom surface (not shown) to attract a set of insertable lenses.

During operation, a user may grasp a set of insertable lenses via the lens-coupling components 522a, 522b and the extensions 521a, 521b may be engaged to transfer the lenses from the tool 520 into eyewear system 550 (having lens casing 510 coupled to the eyewear frame 502) as shown in the figure. In some embodiments, tool 520 may be used to place the insertable lenses into eyewear 550 simultaneously or successively. Although a set of insertable lenses may be inserted manually, tool 550 may be used to reduce human contact with the lenses.

FIG. 6 is a flowchart 600 of a method for enabling a user to assemble an eyewear apparatus consistent with the present disclosure. Flowchart 600 begins with block 601—prompting a user to choose from a plurality of unique frame options. The frame options may be eyewear frames from any of various manufacturers. The user may choose the frames based on style, comfort, etc.

Block 602—prompting the user to choose at least one aesthetic attribute option for the selected frame. For example, the aesthetic attribute option may be one of a color, design, or accessory.

Next, based on the user's selection of the frame, display to the user a plurality of lens casing options (block 603). The lens casings may have any aesthetic design or shape and may give a "flare" to the eyewear system.

Based on the user's selection of the lens casing options, associate the selected frame and lens options to a customer order (block 604). A user may also be prompted to upload a lens prescription. For example, a user may upload a lens prescription such that the eyewear system designed by the user consists of a custom combination of an eyewear frame, lens casing, and prescription lenses. Lastly, the user may be prompted to purchase the order (e.g., checkout).

Systems, methods, and apparatuses describing the present disclosure have been described. It will be understood that the descriptions of some embodiments of the present disclosure do not limit the various alternative, modified and equivalent embodiments which may be included within the spirit and scope of the present disclosure as defined by the appended claims. Furthermore, in the detailed description above, numerous specific details are set forth to provide an understanding of various embodiments of the present disclosure. However, some embodiments of the present disclosure may be practiced without these specific details. In other instances, well known methods, procedures, and components have not been described in detail so as not to unnecessarily obscure aspects of the present embodiments.

What is claimed is:

1. An eyewear system comprising:
   an apparatus and, a pair of eyewear glasses;
   wherein the apparatus comprising:
   a base component, a pair of extensions, a release mechanism, a first lens-coupling component, and a second lens-coupling component;
   wherein the base component comprising an engagement mechanism to engage and disengage the pair of extensions to and from the base component;
   wherein the first lens coupling component coupled to an end of a first extension of the pair of extensions; and
   the second lens coupling component coupled to an end of a second extension of the pair of extensions;
   wherein the first lens-coupling component and the second lens-coupling component are operable to grasp the pair of eyewear lenses and insert the pair of eyewear lenses into a frame of the pair of eyewear glasses;

wherein the first lens-coupling component and the second lens-coupling component each has a shape that is substantially similar to each lens of the pair of eyewear glasses;

wherein the apparatus and the pair of eyewear glasses are individual and separate devices.

2. The eyewear system of claim 1, wherein each of the first lens-coupling component and the second lens-coupling component comprises a magnetic strip.

3. The eyewear system of claim 1, wherein engaged, the pair of extensions can enable a user to assemble at least one eyewear lens of the pair of eyewear lenses into the pair of eyewear glasses.

4. The eyewear system of claim 1, wherein the base component comprises a handle.

5. The eyewear system of claim 1, wherein the pair of extensions are spring-loaded.

6. The eyewear system of claim 1, wherein at least one of the first lens-coupling component or the second lens-coupling component includes a magnetic region that engages with at least one eyewear lens of the pair of eyewear lenses.

7. The eyewear system of claim 1, wherein a distance between the first lens-coupling component and the second lens-coupling component is approximately the same distance between the pair of eyewear lenses installed within the pair of eyewear glasses.

8. The eyewear system of claim 1, wherein the base component has a first side that is coupled to one end of the first extension of the pair of extensions and the base component has a second side that is coupled to one end of the second extension of the pair of extensions.

9. The eyewear system of claim 1, wherein the base component includes a slender handle shaped member that is to facilitate manual handling of the apparatus.

10. The eyewear system of claim 1, wherein the eyewear system further comprising a lens casing; wherein the pair of eyewear lenses are configured to be inserted between the frame of the pair of eyewear glasses and the lens casing which is attached to the frame.

* * * * *